(12) United States Patent
Marshall et al.

(10) Patent No.: US 9,849,243 B2
(45) Date of Patent: Dec. 26, 2017

(54) SUBSTANCE DELIVERY DEVICES

(71) Applicant: OWEN MUMFORD LIMITED, Woodstock (GB)

(72) Inventors: Jeremy Marshall, Oxford (GB); Clive Nicholls, Aylesbury (GB); Stephen Douglas Bicknell, Stratford-Upon-Avon (GB)

(73) Assignee: OWEN MUMFORD LIMITED, Oxfordshire (GB)

( * ) Notice: Subject to any disclaimer, the term of this patent is extended or adjusted under 35 U.S.C. 154(b) by 176 days.

(21) Appl. No.: 15/054,312

(22) Filed: Feb. 26, 2016

(65) Prior Publication Data

US 2016/0175528 A1   Jun. 23, 2016

Related U.S. Application Data

(63) Continuation of application No. 12/096,675, filed as application No. PCT/GB2006/050441 on Dec. 8, 2006, now Pat. No. 9,308,327.

(30) Foreign Application Priority Data

Dec. 8, 2005  (GB) .................................. 0524978.4
Aug. 30, 2006  (GB) .................................. 0617064.1

(51) Int. Cl.
*A61M 5/00*      (2006.01)
*A61M 5/20*      (2006.01)
(Continued)

(52) U.S. Cl.
CPC ...... *A61M 5/2033* (2013.01); *A61M 5/31501* (2013.01); *A61M 5/3202* (2013.01);
(Continued)

(58) Field of Classification Search
CPC ............ A61M 5/2033; A61M 5/31501; A61M 5/3202; A61M 5/326
(Continued)

(56) References Cited

U.S. PATENT DOCUMENTS 3,785,572 A    1/1974   Arnold et al.
4,336,234 A    6/1982   Leutner et al.
(Continued)

FOREIGN PATENT DOCUMENTS

DE    36 38 984 A1    5/1988
DE    195 19 147 A1   12/1995
(Continued)

*Primary Examiner* — Phillip Gray
(74) *Attorney, Agent, or Firm* — Young & Thompson

(57) ABSTRACT

A substance delivery device (autoinjector) for use with a container (such as a syringe) containing the substance includes: a body arranged to house or hold the container; a plunger which is movable with respect to at least a portion of the body, the plunger being arranged to act upon the container so as to move the container with respect to the portion of the body; wherein the plunger is also arranged to expel at least a portion of the substance from the container; and wherein the device includes elements for adjusting the amount of substance to be expelled from the container. The device can also have elements for priming the container, and can accommodate containers of different size or shape.

19 Claims, 8 Drawing Sheets

(51) Int. Cl.
*A61M 5/315* (2006.01)
*A61M 5/32* (2006.01)
*A61M 5/24* (2006.01)
*A61M 5/31* (2006.01)

(52) U.S. Cl.
CPC ............... *A61M 5/326* (2013.01); *A61M 5/24* (2013.01); *A61M 5/3146* (2013.01); *A61M 5/31515* (2013.01); *A61M 5/31553* (2013.01); *A61M 5/31563* (2013.01); *A61M 5/31578* (2013.01); *A61M 5/31591* (2013.01); *A61M 5/3204* (2013.01); *A61M 2005/206* (2013.01); *A61M 2005/2073* (2013.01); *A61M 2005/2407* (2013.01); *A61M 2005/31508* (2013.01); *A61M 2005/3247* (2013.01)

(58) Field of Classification Search
USPC .......................................... 604/208, 232–234
See application file for complete search history.

(56) References Cited

U.S. PATENT DOCUMENTS

| | | | |
|---|---|---|---|
| 4,820,275 A | 4/1989 | Haber et al. | |
| 5,057,086 A | 10/1991 | Dillard, III et al. | |
| 5,114,406 A * | 5/1992 | Gabriel | A61M 5/2033 604/134 |
| 5,176,643 A | 1/1993 | Kramer et al. | |
| 5,271,744 A | 12/1993 | Kramer et al. | |
| 5,405,362 A | 4/1995 | Kramer et al. | |
| 5,514,097 A * | 5/1996 | Knauer | A61M 5/20 604/136 |
| 5,705,112 A | 1/1998 | Gram | |
| 5,807,346 A | 9/1998 | Frezza | |
| 5,833,669 A | 11/1998 | Wyrick | |
| 5,846,042 A | 12/1998 | Iannuzzi | |
| 6,241,709 B1 | 6/2001 | Bechtold et al. | |
| 6,793,646 B1 | 9/2004 | Giambattista et al. | |
| 8,747,367 B2 | 6/2014 | Keitel et al. | |
| 2002/0165500 A1 | 11/2002 | Bechtold et al. | |
| 2004/0186441 A1 | 9/2004 | Graf et al. | |
| 2006/0270985 A1 | 11/2006 | Hommann et al. | |
| 2006/0270986 A1 | 11/2006 | Hommann et al. | |
| 2007/0027430 A1 | 2/2007 | Hommann | |
| 2007/0197975 A1 | 8/2007 | Burren et al. | |
| 2007/0233009 A1 | 10/2007 | Kirchhofer | |
| 2008/0208123 A1 | 8/2008 | Hommann | |

FOREIGN PATENT DOCUMENTS

| | | |
|---|---|---|
| DE | 199 48 988 A1 | 4/2000 |
| EP | 0 073 356 A1 | 3/1983 |
| EP | 1 228 777 A1 | 8/2002 |
| JP | 55-116620 A | 9/1980 |
| JP | 63-139563 A | 6/1988 |
| JP | 2003-511157 A | 3/2003 |
| WO | 92/19296 A2 | 11/1992 |
| WO | 94/26331 A1 | 11/1994 |
| WO | 99/38554 A1 | 8/1999 |
| WO | 00/62839 A2 | 10/2000 |
| WO | 01/26710 A2 | 4/2001 |
| WO | 03/008023 A1 | 1/2003 |
| WO | 03/011378 A1 | 2/2003 |
| WO | 2005/009515 A1 | 2/2005 |
| WO | 2005/044346 A2 | 5/2005 |
| WO | 2005/044347 A1 | 5/2005 |
| WO | 2005/046770 A1 | 5/2005 |
| WO | 2005/058396 A1 | 6/2005 |
| WO | 2005/097238 A2 | 10/2005 |
| WO | 2005/102419 A1 | 11/2005 |
| WO | 2006/021110 A1 | 3/2006 |
| WO | 2006/062997 A1 | 6/2006 |
| WO | 2006/122437 A1 | 11/2006 |

* cited by examiner

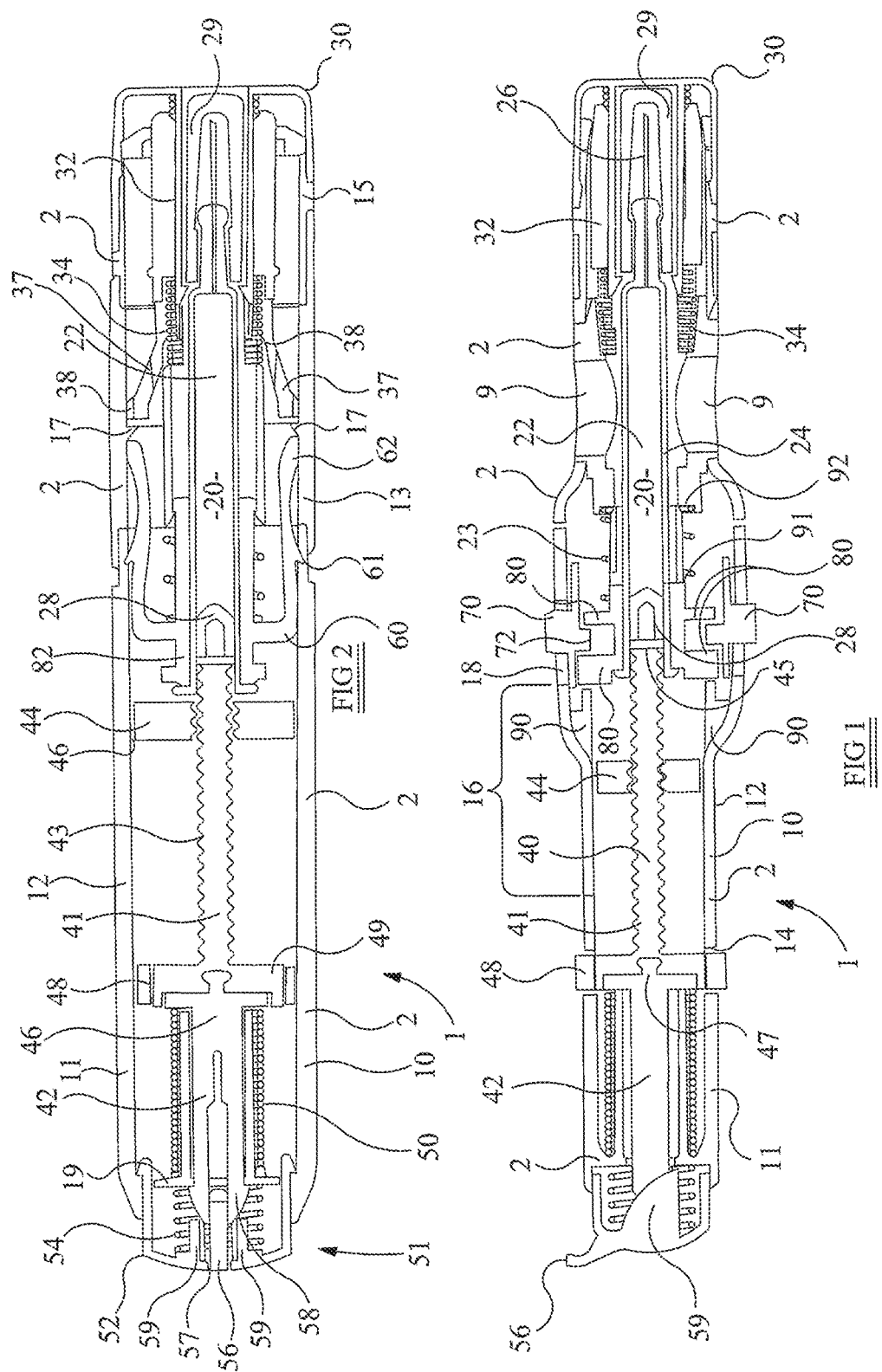

SUBSTANCE DELIVERY DEVICES

FIELD OF THE INVENTION

The present invention relates to substance delivery devices (e.g. injection devices) and parts thereof, in particular an adjustment mechanism for use in such devices.

SUMMARY OF THE INVENTION

Although not limited thereto, the present invention finds particular application in substance delivery devices (in particular drug delivery devices) which are intended to house, or include, a container which, during the delivery process, is moved in distal direction so that the container is moved towards the skin of a patient, whereby the movement of the container is followed by a substance contained in the container being expelled. The container can for example be a syringe so that, when the container (syringe) moves in distal direction, the needle of the syringe penetrates the skin of the patient so that the substance in the syringe is subsequently injected into the patient. As used in the present specification, the term "distal" is intended to designate a location or direction towards the (injection site of the) patient's skin, and the term "proximal" is intended to designate a location or direction away from the (injection site of the) patient's skin.

The substance to be expelled will in most cases be a fluid, in particular a liquid. It is however conceivable that the substance could comprise a powder, suspension or similar, or a mixture of any of these substances. The container can also comprise a dual chamber cartridge, e.g. with a liquid in one chamber and a powder in the other which are mixed just prior to being expelled. For the sake of simplicity the description will proceed using fluid as an example of the substance to be expelled, and a syringe with needle will be used as an example of a container, but it will be appreciated that the invention encompasses applications without needle.

BACKGROUND OF THE INVENTION

Many injection devices of the above type (i.e. where a syringe is moved in distal direction during the injection operation) are particularly easy to use since the entire injection process (causing the needle of the syringe to penetrate the skin and the dose to be injected) can be triggered simply by pushing one button. One example of such an injection device is disclosed in WO 03/011378, which is incorporated herein by reference in its entirety. Whilst this device works well, the present inventors have appreciated at least two drawbacks with this device: there is no provision for adjusting the dose to be injected, and there is also no provision for priming the syringe. By way of explanation, "priming" refers to the process of expelling from the syringe any air and perhaps a small amount of fluid which is initially contained in the syringe. The present invention has been made with a view to overcoming these drawbacks. However, it will be appreciated, on consideration of the present specification, that the various aspects of the invention find application also in other types of injection/substance delivery devices.

Whilst dose adjustment and a priming function are generally known (the attention of the reader is directed to WO 2005/044346 and WO 2005/046770, also incorporated herein by reference in their entirety), it will be appreciated that thus far there has not been any attempt to provide the injection device of e.g. WO 03/011378 with an adjustment and/or priming function. As will be appreciated, the way in which the adjustment and the priming function pursuant to the present invention work is quite different from any adjustment or priming function disclosed in WO 2005/046770 and WO 2005/044346. This is why in particular the dose adjustment mechanism is useful in its own right, that is, it can be used with a range of other injection devices, not limited to injection devices in which a syringe is moved in distal direction during the injection process.

Aspects of the invention are set out in the independent claims.

BRIEF DESCRIPTION OF THE DRAWINGS

Some preferred embodiments of the invention will now be described by way of example only and with reference to the accompanying drawings, in which:

FIG. 1 shows a longitudinal section through an injection device according to a first embodiment of the present invention.

FIG. 2 shows a longitudinal section through the injection device shown in FIG. 1, whereby the section plane of the FIG. 2 view is perpendicular to the section plane of the FIG. 1 view.

DETAILED DESCRIPTION OF THE INVENTION

Figure 3:
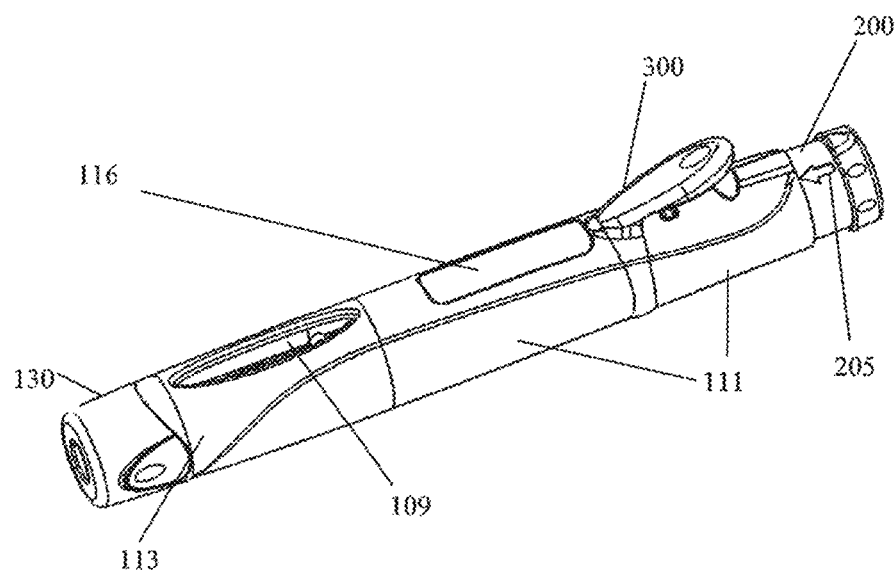
FIG. 3 shows a perspective view of an injection device according to a second embodiment of the present invention.

The injection device 1 shown in section in FIG. 1 is shown in a condition before use. FIG. 2 shows the same device, also before use, but sectioned at 90° to the FIG. 1 view.

Referring both to FIGS. 1 and 2 (not all reference numbers are shown in both Figures), the injection device 1 comprises a body or housing 2, which has three portions. These are (in the order from the proximal end of device 1 to the distal end): a main body 10, a mid body 13 and a shroud retainer 15, the main body 10 is subdivided into a proximal main body portion 11 and a distal main body portion 12. These portions can be formed as one piece. The housing 2 carries or houses a sleeve-like syringe carrier 82, which in turn carries a syringe 20. Syringe 20 comprises a generally cylindrical container portion 24 for accommodating a fluid 22, and a needle 26. The needle is in communication with the interior of container portion 24 so that the fluid 22 may be expelled through needle 26. A bung 28 is inserted in the container portion 24 at the proximal end. This prevents leakage of the fluid 22 out of the proximal end of container portion 24. Syringe 20 is biased towards the proximal end by means of spring 23. This spring is however relatively weak. Needle 26 is initially protected by a needle sheath 29.

A safety cap or needle sheath remover 30 is provided at the distal end of injection device 1. This safety cap is carried by a shroud retainer 15 of housing 2. Towards its proximal end the safety cap is hooked over the proximal end of needle sheath 29 so that, when safety cap 30 is removed, the needle sheath is removed as well.

The distal end of injection device 1 is also provided with a needle guard 32 or "lockout shroud". This needle guard is movable along the longitudinal axis of the injection device over a limited range. The needle guard 32 is however initially covered, and prevented from moving, by safety cap 30. Only once safety cap 30 has been removed (as will be explained below) can needle guard 30 move.

Towards the proximal end of injection device 1 there is provided a plunger 40, which has a distal portion 41 and a proximal portion 42. The plunger is biased by spring 50 towards the distal direction. This bias is relatively strong, and much stronger than the bias provided by spring 23.

At the very proximal end of injection device 1 there is provided a firing button assembly 51. Its structure and function will be explained below.

The core principle of operation and much of the structure of the injection device 1 is very similar to the technique disclosed in WO 03/011378. Essentially, as in that earlier document, after removal of the safety cap 30 (and needle sheath 29) the needle guard 32 extends in distal direction because of the bias provided by spring 34. The distal end of the injection device 1 is then pressed against a patient's skin. This pushes needle guard 32 in proximal direction against the bias of spring 34. However, during this action the needle 26 does not project beyond the distal end of needle guard 30.

As in the earlier-disclosed technique, when the firing button is depressed the plunger is released and can move in distal direction. When the front surface 45 of plunger 40 contacts bung 28, continued movement of the plunger in distal direction initially moves syringe 20 (i.e. not just bung 28) in distal direction. This is so because the force required to move bung 28 in distal direction with respect to container portion 24 is greater than the force required to move the entire syringe 20 in distal direction (to this end the interior surface of the container portion 24 can be provided with circumferential ribs or other friction increasing formations). During this movement of syringe 20 the needle 26 penetrates the skin of the patient. Eventually the movement in distal direction of syringe 20 comes to a halt, but plunger 40 is still able to move further in distal direction. This leads to bung 28 being moved in distal direction with respect to container portion 24, which means that fluid 22 is expelled from container portion 24 through needle 26 into the patient. Hence the movement of the syringe 20 (as a whole) and the movement of bung 28 within syringe 20 is brought about by plunger 40 acting on bung 28. It will be appreciated that the portion of plunger 40 (i.e. distal end surface 45) which acts on the syringe 20 to move the syringe is the same as the portion of the plunger which acts on the syringe to move bung 28 so as to expel the fluid. When the plunger 40 has its movement in distal direction stopped the injection operation has been completed. The user can then move the injection device 1 in proximal direction so as to withdraw the needle from the injection site. As the injection device 1 is withdrawn from the skin of the patient the needle guard 32 is moved in distal direction due to the bias provided by spring 34. The guard 32 then locks in the distal position rendering the device safe. The injection device 1 can then be disposed of.

In contrast to the earlier-disclosed injection device, the injection device shown in FIGS. 1 and 2 has several additional features. Most notably these additional features are an adjustment means for adjusting the dose to be injected, and a priming function.

The adjustment means primarily comprises a stop member 44 which is carried by the distal plunger portion 41. Stop member 44 is, in the preferred embodiment, provided with an internal thread co-operating with an external thread 43 on the circumferential surface of the distal plunger portion 41. Additionally, stop member 44 is keyed at 46 to the inner surface of distal housing portion 12. With stop member 44 being threadibly engaged with the distal plunger portion 41 and being keyed to distal housing portion 12 (e.g. by means of splines or similar, not shown), the stop member 44 will move in distal or proximal direction when distal plunger portion 41 is rotated about its longitudinal axis.

Distal plunger portion 41 can be rotated by means of adjustment ring 48. Adjustment ring 48 is keyed to a relatively large diameter proximal portion 49 of the distal portion 41 of plunger 40. This means that, on rotation of adjustment ring 48, the distal plunger portion 41 will carry out the same rotation, but the distal plunger portion 41 is substantially free to move in a direction parallel to the plunger axis, independently from adjustment ring 48. The proximal portion 49 of the distal plunger portion 41 is engaged with the distal portion 47 of the proximal plunger portion 42 such that the distal plunger portion 41 can substantially freely rotate with respect to the proximal plunger portion 42 but has to make the same movements in distal or proximal direction as the proximal plunger portion 42.

The adjustment ring 48 is located between proximal and distal main body portions 11 and 12. Windows 14 are provided on opposite sides of main body 10 where the proximal and distal main body portions 11 and 12 meet.

The injection device 1 has a generally oval cross section. The windows 14 are provided on those "sides" of the oval which have the smaller distance from the centre of the oval. The main body is continuous on those "sides" of the oval which have the greatest distance from the centre of the oval. This means that the main body 10 with proximal and distal main body portions 11 and 12 can be formed (e.g. moulded) in one piece and further that adjustment ring 48 can project through windows 14 whilst being securely held within main body 10.

In order to adjust the dose to be injected the user can rotate adjustment ring 48, thereby rotating the distal portion 41 of plunger 40. As mentioned, this sets the axial position of stop member 44 along distal plunger portion 41. Through setting this axial position the user can determine how far the plunger is allowed to project into container portion 24. This is so because movement of the plunger in distal direction during the injection process is stopped when stop member 44 makes contact with the proximal end of container portion 24. The axial position of stop member 44 along distal plunger portion 41 (before the beginning of the injection operation) can be viewed by the user through a further window 16 provided in the distal main body portion 12. Suitable indications may be provided at window 16 to indicate to the user which dose corresponds to the set position of stop member 44 with respect to window 16.

While FIGS. 1 and 2 show the injection device 1 generally in the same state, it will be noted that the position of stop member 44 is different in these two Figures. Stop member 44 has been moved in proximal direction in FIG. 1 so as not to obscure any details.

Turning now to the priming function of injection device 1, two priming buttons 70 are provided in the distal housing portion 12 (it is to be noted that the priming function could be achieved with only one priming button, but two priming buttons are preferred). Priming buttons 70 can be slid parallel to the longitudinal axis of injection device 1 over a small distance determined by the length of window 18. A projection 72 is provided on the radially inner side of each priming button 70, which projection engages with engagement formations 80 of the syringe carrier 82 around container portion 24. The co-operation between projection 72 and engagement formations 80 means that, initially, the syringe carrier 82 is locked against axial movement with respect to priming buttons 70. Container portion 24 in turn is sufficiently firmly attached to syringe carrier 82, which means that syringe 20 is also locked against axial movements with respect to priming buttons 70. The priming buttons may be formed such that accidental priming can be prevented. For example, priming buttons 70 may be formed with a catch or similar (not shown) so that they must be depressed before they can be moved in proximal direction.

In order to prime syringe 20 a user would hold injection device 1 upright so that the distal end points upwards. The user then moves priming buttons 70 in proximal direction (i.e. downward) until the priming buttons 70 contacts the proximal ends of windows 18. Syringe carrier 82 and syringe 20 perform the same proximal movement. As a result of this proximal movement the bung 28 is pushed in distal direction with respect to container portion 24 as its proximal end contacts the distal end 45 of the distal plunger portion 41. Any air contained in container portion 24 is thus expelled through needle 26 (and perhaps also a small amount of fluid 22).

As syringe 20 and syringe carrier 82 move in proximal direction the syringe carrier 82 is pivoted slightly about the axis of the syringe. This pivoting movement is achieved by a camming arrangement at the proximal end of syringe carrier 82. The camming arrangement comprises cam surfaces at the proximal end of syringe carrier 82 and a corresponding cam surface provided at the distal end of projections or ribs 90 which are provided on the inside of distal main body portion 12. As these cam surfaces contact and slide along each other the syringe carrier 82 is pivoted. This pivoting movement has the effect that syringe carrier 82 (and therefore also syringe 20) is no longer locked against axial movement with respect to priming buttons 70 since internal projections 72 and the engagement formations 80 on the syringe carrier 82 are limited in circumferential direction. This means that, once syringe carrier 82 has turned, the engagement formation 80 can freely move past internal projection 72 so as not to impede or prevent the injection operation. The syringe 20 may turn with syringe carrier 82 during priming, although this is not essential.

The way in which the priming function is implemented means that the injection operation cannot normally be performed without the priming operation having been performed first since without the priming operation having been performed the syringe 20 cannot move in distal direction since it is locked with respect to priming buttons 70, which in turn are prevented from moving in distal direction as they contact the distal ends of windows 18.

In preferred embodiments the projections or ribs 90 and most of the structure of priming buttons 70 (preferably all of the structure of priming buttons 70, apart from their internal projections 72) are accommodated in an enlarged diameter portion of the distal main body portion 12. This can ensure that, once the priming operation has been completed, the projections or ribs 90 and the priming buttons 70 do not interfere with stop member 44 when plunger 40 moves in distal direction.

However, in alternative embodiments no such enlarged diameter portion of distal main body portion 12 is provided and the projections or ribs 90 and much of the structure of priming buttons 70 project into distal main body portion 12. In those embodiments the stop member 44 is provided with recesses at the circumferential positions of projections 90 (and priming buttons 70) so that stop member 44 can move past projections 90 and priming buttons 70 when plunger 40 and stop member 44 move in distal direction. Interference between plunger 40 and projections 90 or priming buttons 70 can thus be avoided. The recesses (not shown) in stop member 44 could conveniently be used as part of a recess and spline arrangement for keying stop member 44 with respect to main body 10.

Mid body 13 is provided with two viewing windows 9 on opposite sides so as to permit a user to view container 24. In the preferred embodiment the viewing windows 9, the windows 14 and the windows 16 are all provided on the same side(s) of the housing 2. Whilst it is preferred that two opposing ones of each type of window 9, 14 and 16 are provided, the device 1 may also be formed with only one, or more than two of each type of window 9, 14 and 16.

The firing button arrangement 51 will now be explained, although it will be appreciated that alternative firing arrangements could be used. The firing button arrangement 51 comprises a firing button 52 carried by, and slidable within, the proximal end of the proximal main body portion 11. In the initial position however the firing button 52 is not slidable. The reason for this is as follows. At the proximal end of the proximal plunger portion 42 there are provided two or more fingers which are provided with outwardly projecting teeth or plunger retaining barbs indicated by 58. These outwardly projecting teeth 58 butt against a shoulder 19, which is firmly attached to proximal main body portion 11 or is formed integrally thereto. This prevents the proximal plunger portion 42 from moving in distal direction. A safety tab 56 is provided at the centre of firing button 52, and the distal end of the safety tab 56 also butts against shoulder 19. This prevents safety button 52 from being depressed. When the injection device is to be used the user would tear safety tab 56 off (it is connected to firing button 52 by a thin bridge 57, which is easily severed) and remove the safety tab 56 from the firing button 52. This enables firing button 52 to be depressed in distal direction against the bias of spring 54. Firing button 52 is provided with at least one internal projection 59, preferably an annular projection 59, which is arranged to squeeze the fingers at the proximal end of proximal plunger portion 41 together so that teeth 58 have cleared shoulder 19. Plunger 40 is thus released, which enables it to perform the injection operation.

At the end of the injection operation syringe carrier 82 has moved in distal direction such that a set of locking barbs 61 has moved in distal direction past a set of housing barbs 17. Housing barbs 17 are provided on an internal surface of mid body portion 13 whilst locking barbs 61 are provided on flexible legs 60 formed integrally with syringe carrier 82. Locking barbs 61 project outwardly so that they can engage housing barbs 17 to prevent syringe carrier 82 from moving in proximal direction after the injection operation has been completed.

Locking barbs 61 and housing barbs 17 have the following purpose. When the injection device 1 has been pressed against a patient's skin the needle guard 32 will have moved in proximal direction (to the position shown in FIGS. 1 and 2, since needle guard 32 will have moved in distal direction as soon as safety cap 30 has been removed, due to the bias provided by spring 34). During the injection operation, as syringe carrier 82 moves in distal direction, the distal ends 62 of legs 60 move inwardly, using the proximal surface of housing barbs 17 as a ramp. This enables legs 60 to slide between and through guard legs 38 attached proximally to needle guard 32 (guard legs 38 are provided with an opening 37 so that legs 60 can project into/through guard legs 38). Eventually, legs 60 come to a halt between guard legs 38 when the syringe carrier 82 has completed its movement in distal direction due to a stop surface 91 of syringe carrier 82 stopping against a stop feature 92 of mid body 13. After the injection operation, when injection device 1 is withdrawn from the injection site, needle guard 32 moves in distal direction, due to the bias provided by spring 34. While this happens the guard legs 38 slide in distal direction past the distal ends 62 of legs 60, and whilst syringe carrier 82 does not move in axial direction legs 60 move outwardly as they are no longer biased inwardly by guard legs 38. Once legs 60 have moved outwardly the locking barbs 61 are approximately at the same radial position as housing barbs 17 but slightly more distal than housing barbs 17, which means that syringe carrier 82 cannot be moved in proximal direction beyond a position where locking barbs 61 engage housing barbs 17.

If, once legs 60 have moved outwardly, any attempt is made to move needle guard 32 in proximal direction, then the proximal end of guard legs 38 will butt against the distal end 62 of legs 60. Because of this (syringe carrier 82 being prevented from movement in proximal direction because of the engagement of locking barbs 61 and housing barbs 17) the needle guard cannot be moved any further in proximal direction. This ensures that the needle 26 cannot be caused to project beyond the distal end of needle guard 32 after the injection device 1 has been used.

The injection device 1 is particularly easy to use. In order to perform an injection operation a user would "work their way up" along the injection device 1, starting at the distal end. Initially, the user would remove the safety cap 30. The user would then prime the syringe by means of priming buttons 70, then set the desired dose by turning adjustment ring 48, then remove the safety tab 56, then press the injection device against the skin and then press the firing button 52. After the injection operation the user would withdraw the injection device 1 from the skin and dispose of the device.

The injection device 1 can also accommodate different syringe diameters (i.e. sizes) with minimal modifications. If a smaller diameter syringe is desired to be used, then syringe carrier 82 should have a relatively small bore in which to accommodate the syringe. If a larger diameter syringe is to be used, then the bore of syringe carrier 82 should be made larger. Accordingly, a range of syringe carriers 82 with different bore diameters can be provided for use with the injection apparatus. All other parts of the injection apparatus may be the same for any syringe diameter (of course, the diameter of the distal plunger portion needs to be sufficiently small so that the plunger can project into container portion 24). This enables all parts of the injection device 1 (apart from the syringe carrier 82) to be manufactured in large numbers at reduced cost Whilst the present invention has been described using a preferred embodiment as an example, it will be appreciated that the invention is not limited to a device having all of the features of the embodiment described with reference to FIGS. 1 and 2. In particular, it will be appreciated that the dose adjustment mechanism may be useful in its own right, and can be used in connection with other kinds of injection devices.

A second embodiment of the present invention will now be described with reference to FIGS. 3 to 16. Many features, as well as a major part of the principle of operation, of the second embodiment correspond to, or are similar to, those in the first embodiment described with reference to FIGS. 1 and 2 and will therefore not necessarily be described again in detail. Features in FIGS. 3 to 16 which are similar to corresponding features in FIGS. 1 and 2 carry a reference numeral between 100 and 199, whereas features whose structure or position is not necessarily similar to that in FIGS. 1 and 2 carry reference numerals from 200 onwards.

FIG. 3 shows a perspective view of the injection device according to the second embodiment. This includes a housing with a mid body 113 and a proximal main body portion 111. Mid body 113 may be held with respect to proximal main body portion 111 by means of unidirectional teeth 450 (shown in FIG. 13) or other "snap features". A safety cap 130 is located at the distal end of the injection device. A syringe viewing window 109 is formed in mid body portion 113, and a dose indicator window 116 is provided in proximal main body portion 111. Both viewing windows can be left open, but are preferably covered by a transparent material so as to protect the interior of the device.

The priming, dose adjustment and trigger functions are somewhat different from those of the first embodiment. A combined priming button and dose dial 200 is provided at the proximal end of the injection device. A priming alignment arrow 205 is marked on the priming button 200. A trigger (or firing button) 300 is mounted to the body, laterally along proximal main body portion 111.

Figure 4:
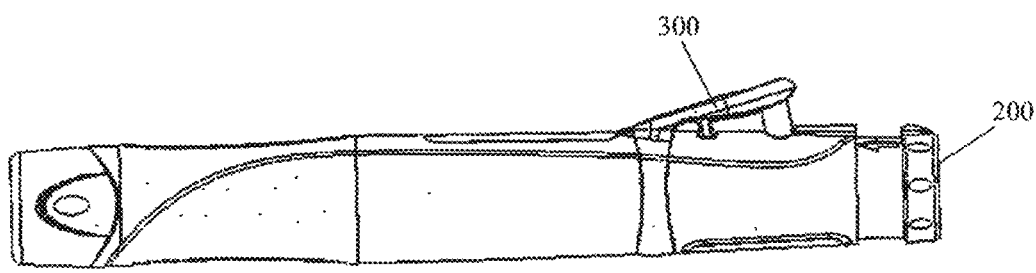
FIG. 4 shows a side view of the embodiment shown in FIG. 3.
Figure 5:
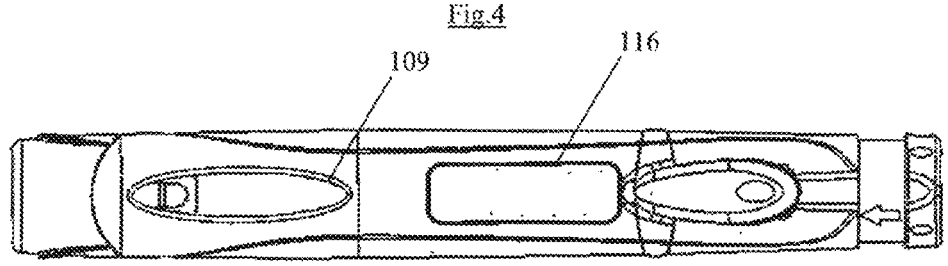
FIG. 5 shows a top view of the embodiment shown in FIG. 3.

FIGS. 4 and 5 show the injection device according to the second embodiment from the side and from the top.

Figure 6:
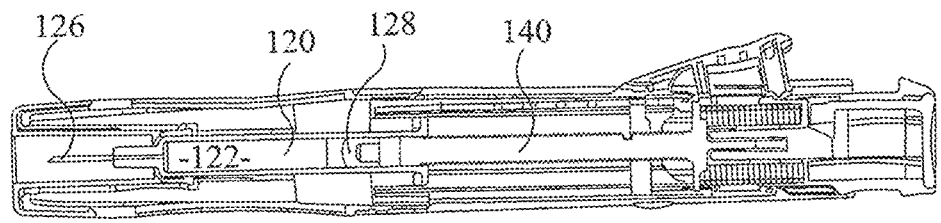
FIG. 6 shows a longitudinal section through the embodiment shown in FIG. 3.

The sectional view of FIG. 6 shows the interior structure of the injection device. As in the first embodiment, the injection device includes a syringe 120 containing liquid 122, a needle 126 mounted to the distal of syringe 120, a bung 128 and a plunger 140.

Figure 7:
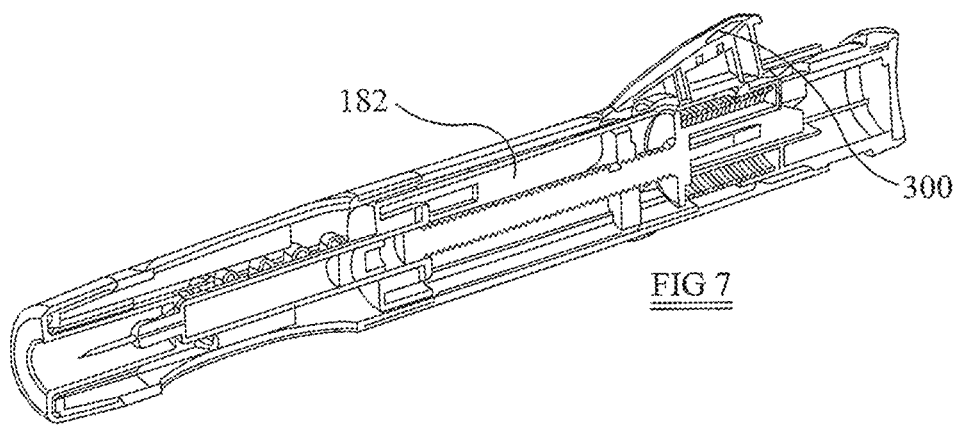
FIG. 7 shows a perspective view of the sectional view of FIG. 6.

As shown in FIG. 7, a syringe carrier 182 is located within the housing, generally within proximal main body portion 111. Syringe carrier 182 carries syringe 120 such that syringe 120 can only be moved in distal direction when syringe carrier 182 also moves in distal direction.

Figure 8:
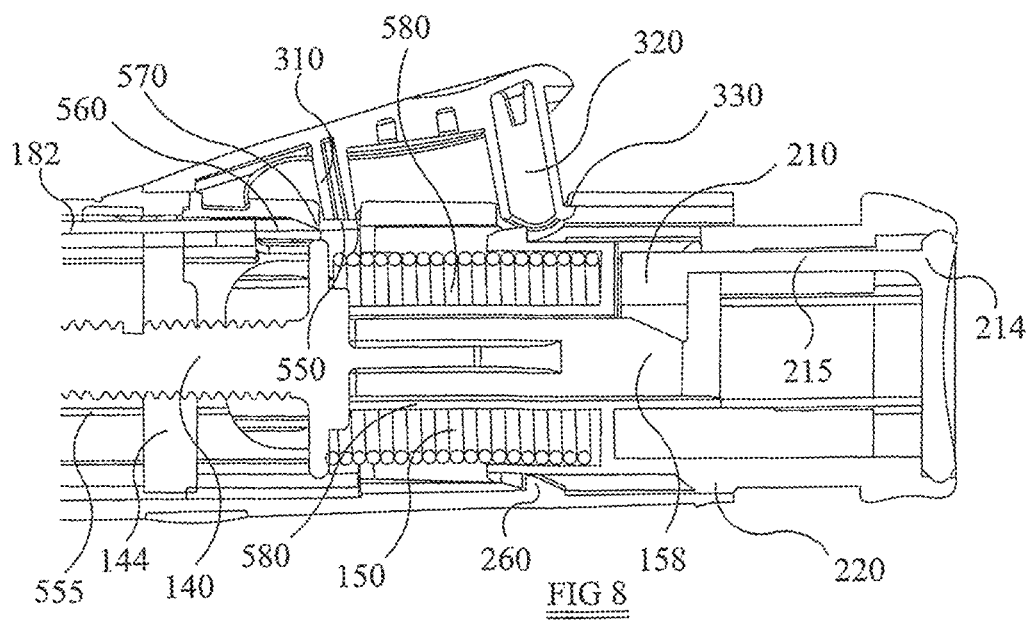
FIG. 8 shows a longitudinal section through the proximal portion of the embodiment shown in FIG. 3.

FIG. 8 shows the structure of the proximal portion of the injection device in more detail. The priming button 200 is held slideably within proximal main body portion 111. It is prevented from sliding in proximal direction out of the housing by means of snap teeth 260. For example three of these snap teeth may be provided, spaced equally around the housing. The priming button 200 is however initially also prevented from moving in distal direction, as will be described later. As will also be described later, angular movement of priming button 200 is initially also restricted, for example to a movement of 30°. A spring 150 is compressed between a distal surface of priming button 200 and a proximal surface of plunger 140. Plunger 140 is thus biased in distal direction. However, plunger 140 is prevented from moving in distal direction since it is firmly connected or integrally formed with two fingers with outwardly projecting teeth 158 (somewhat similar to the two fingers and teeth 58 of the proximal plunger portion 42 shown in FIG. 2. Whilst not explicitly shown in FIG. 8, teeth 158 are "hooked" over a proximal surface of priming button 200.

At its distal end the priming button 200 forms a non-circular channel 580, preferably of square cross section. The fingers of the plunger are of a corresponding cross section and pass through channel 580 so that the fingers (i.e. plunger 140) substantially cannot rotate with respect to channel 580. Plunger 140 is thus angularly locked with priming button 200.

A firing block 210 forms part of priming button 200. In the embodiment shown in FIG. 8 the firing block is moulded into a trim cap 214 of priming button 200 and connected to the proximal portion of trim cap 214 by means of a flexible leg 215.

Radially inwardly the firing block 210 is provided with a "V" shaped cut out, i.e. in a cross sectional view perpendicular to the axis of the device the firing block has a generally "V" shape. The proximal end of teeth 158 is received within the "V" shape.

Figure 9:
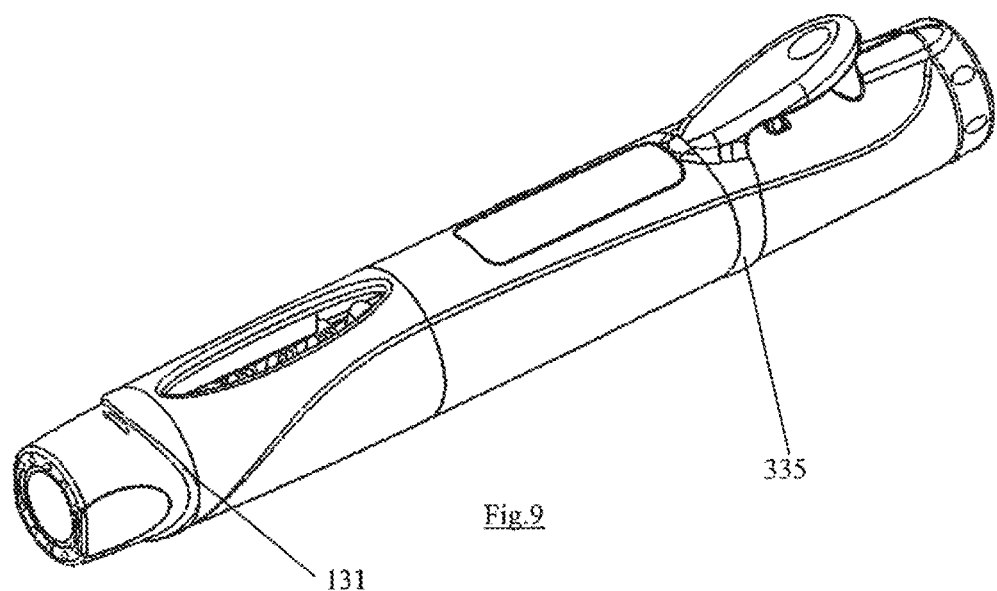
FIG. 9 shows a perspective view of the embodiment shown in FIG. 3, after priming.
Figure 10:
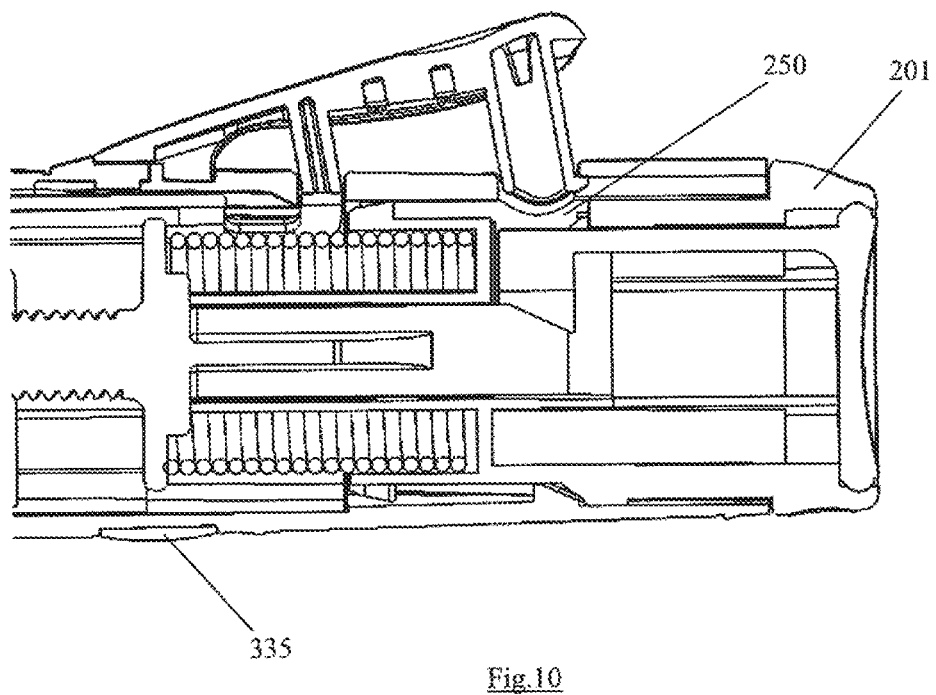
FIG. 10 shows a longitudinal section through the proximal portion of the embodiment shown in FIG. 3, after priming.

The trigger 300 is pivotally connected to the housing, as also shown in FIG. 9. As shown in FIG. 9, the trigger may be provided with a ring 335, which is attached into a recess around the outside of the device, approximately mid-way along the proximal main body portion 111. Referring again to FIG. 8, a syringe carrier release pin 310 projects from approximately mid-way along trigger 300 radially inwardly. A firing pin 320 projects from near the proximal end of trigger 300, also radially inwardly. Whilst trigger 300 is formed such that it can in principle be pivoted and/or flexed inwardly, it is initially prevented from doing so by the distal portion of priming button 200, which blocks the inward path of travel of firing pin 320. Trigger 300 is held in place by a tooth 330 projecting in proximal direction from the radially inner end of firing pin 320.

The syringe carrier 182 is located within the housing. As is more clearly shown in FIG. 15, syringe carrier 182 is provided with an opening or recess 560 near its proximal end. A bridge portion 550 is located proximally adjacent the opening or recess 560. A tooth 570 formed radially inwardly on proximal main body portion 111 projects into opening or recess 560, as shown in FIG. 8. The distal surface of bridge portion 550 butts against the proximal surface of tooth 570 so that syringe carrier 182 is prevented from moving in distal direction. Whilst it is preferred that syringe carrier 182, while being held by tooth 570, cannot move at all in distal direction, it would also be possible to provide a small gap between tooth 570 and bridge portion 550 so that syringe 182 can move over a very limited range in distal direction.

As in the first embodiment, plunger 140 has an externally threaded shaft, onto which internally threaded stop member 144 is threaded. As shown in more detail in FIG. 11, stop member 144 has at least one projection 410 which is guided by an internal rib 555 extending longitudinally along a portion of syringe carrier 182. Preferably at least two projections 410 and ribs 555 are provided so that stop member 144 is prevented from rotating with respect to syringe carrier 182. On rotation of plunger 140 the stop member 144 will thus travel longitudinally along the threaded portion of plunger 140.

Operation of the second embodiment will now be described. Initially, the user would remove the safety cap 130 either by simply pulling it in distal direction, or by rotating it and then pulling it in distal direction. A cam 131 is formed between the proximal end of safety cap 130 and the distal end of mid body portion 113. This can help to overcome any particular high forces which may occur if the needle sheath (see item 29 in FIGS. 1 and 2) sticks to the syringe 120. In contrast to the first embodiment, after removal of the safety cap 130 no needle guard moves in distal direction. The needle 126 remains protected by, and within, the shroud 132 shown in more detail in FIG. 15.

The safety cap 130 should be removed prior to priming so that air can be expelled from syringe 120 during priming.

As mentioned above, initially the priming button 200 is prevented from moving in distal direction (as will be explained later). After removing safety cap 130 the user would pivot priming button 200 by about 30°. After this pivoting movement the priming button can be moved to a limited extent in distal direction (details of this movement in distal direction will be explained later). During the movement in distal direction the priming button 200, which butts against plunger 140, pushes plunger 140 in distal direction. Assuming that the injection device is held in a generally upright position, with the distal end pointing upwards, the syringe 120 will be primed during the movement of the plunger 140 in distal direction since the plunger moves bung 128 further into the syringe 120. In order to achieve proper priming it is preferable that, in the initial condition, the distal surface of plunger 140 is close to, or butts against, the proximal surface of bung 128. During priming the syringe does not move with respect to the housing since syringe 120 is held within syringe carrier 182 which itself is prevented from moving in distal direction, as described above. Instead, the plunger 140 moves with respect to the housing.

After priming the injection device is in the condition shown in FIG. 9, which shows that safety cap 130 has been removed and that the priming button 200 has moved in distal direction.

The user would then set the required dose. Once the device has been primed the user can fully rotate the dose dial 201 (see FIGS. 10 to 12) at the proximal end of priming button 200. Rotating the dose dial 201 rotates the entire priming button 200, including the square channel 580. As plunger 140 is rotationally locked to square channel 580 the plunger will rotate as well. This in turns moves the stop member 144 in longitudinal direction. The closer the stop member 144 is moved towards the syringe 120 the less is the extent to which plunger 140 can project into syringe 120, i.e. the less will be the dose dispensed.

After the dose has been set the user would hold the distal end of the injection device against the desired injection site on the patient's skin (the patient may be the same as the user).

Figure 11:
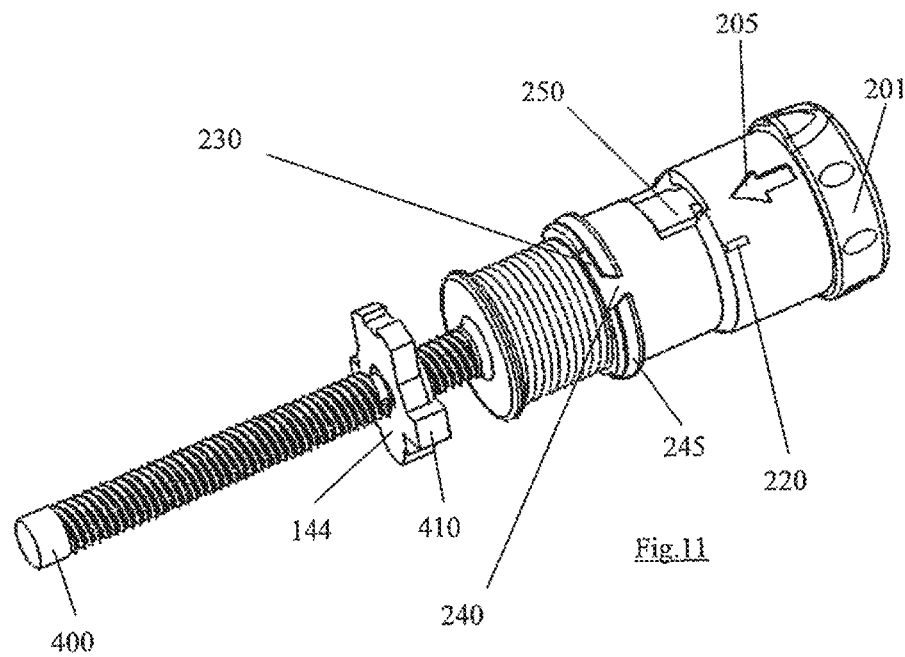
FIG. 11 shows a perspective view of a sub-assembly of the embodiment shown in FIG. 3.
Figure 12:
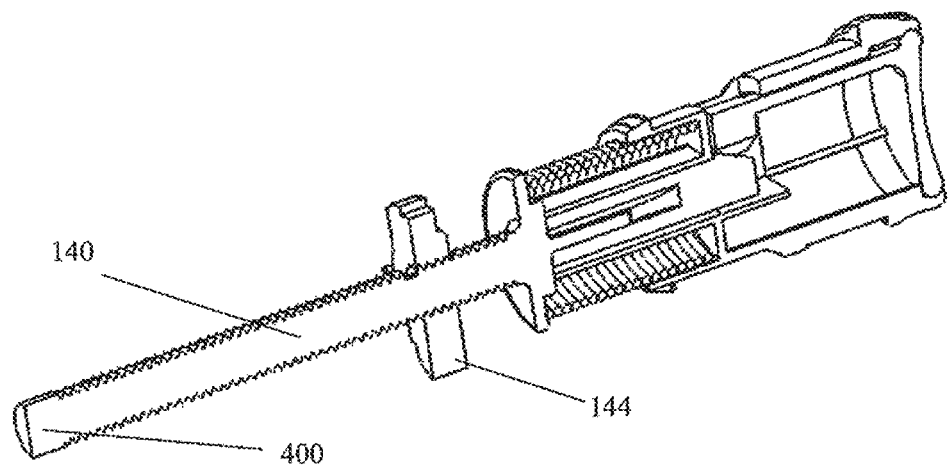
FIG. 12 is a perspective view of a longitudinal section through the sub-assembly shown in FIG. 11.
Figure 13:
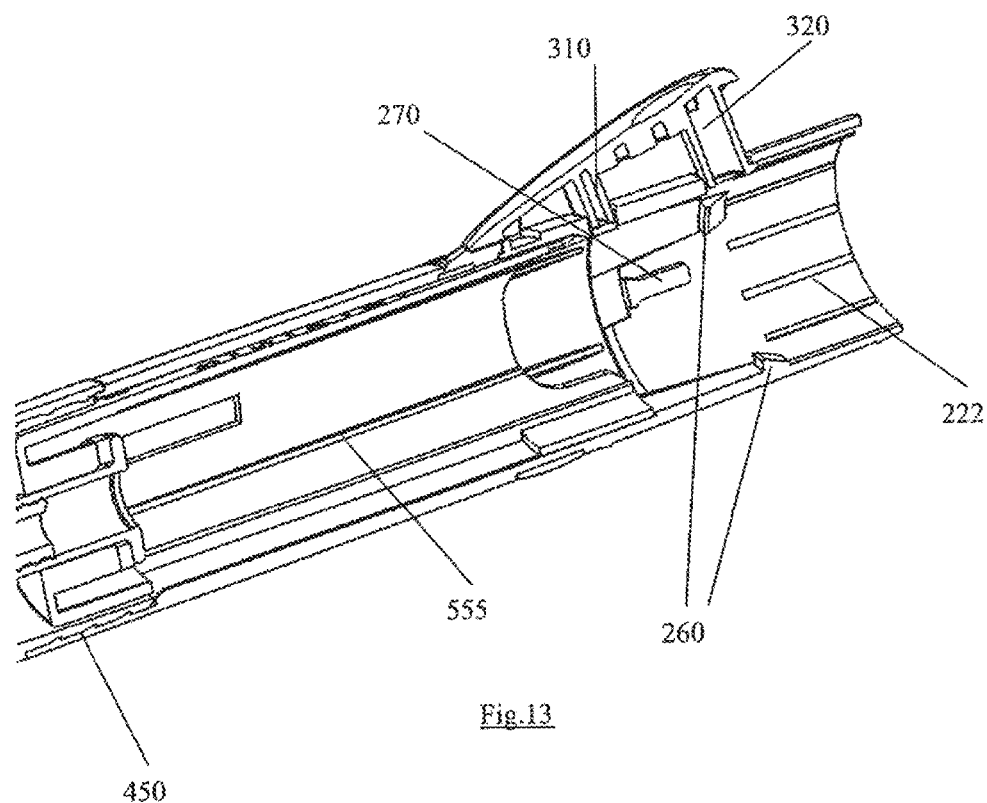
FIG. 13 shows a perspective view of a longitudinal section through part of the body of the embodiment shown in FIG. 3.

The priming button 200 is formed with a window 250 which needs to be aligned with firing pin 320 so that trigger 300 can be pivoted towards the housing. In order to better indicate to the user that the dose dial is in the "correct" position (i.e. so that window 250 is aligned with firing pin 320) the priming button 200 can be provided, as shown in FIG. 11, with one or more ribs 220 which is/are accepted in one or more recesses 222 in the proximal main housing portion 111, as shown in FIG. 13.

Additionally, markings on the surface of the proximal main housing portion and on the dose dial 201 may be provided which, when aligned, indicate alignment of window 250 and firing pin 320.

Once the window 250 has been aligned with firing pin 320 the user can depress the trigger 300. As trigger 300 is depressed the syringe carrier release pin 310 presses down bridge portion 550, which moves radially inwardly so that it is no longer held by tooth 570 of the proximal main housing portion 111. This means that the syringe carrier (and with it the syringe) can move in distal direction. Further, as trigger 300 is pivoted inwardly it pushes firing block 210 inwardly as well. The inward movement of firing block 210 squeezes the proximal end of fingers 158 together so that they no longer project laterally beyond the internal edge of the square channel 580, i.e. the plunger 140 is no longer prevented from moving in distal direction. The force stored in compression spring 150 thus propels plunger 140 in distal direction so that the actual injection operation can begin, similar to the first embodiment. As plunger 140 moves in distal direction it acts on bung 128. Since the force required to move bung 128 with respect to syringe 120 is greater than the force required to move the syringe 120 and syringe carrier 182 in distal direction the movement of plunger 140 initially only moves the syringe and syringe carrier in distal direction, substantially without expelling any drug from syringe 120. Syringe carrier 182 is free to move in distal direction since the syringe carrier release pin 310 has released it from tooth 570. The movement of the plunger and syringe carrier in distal direction continues until the distal surface of syringe carrier 182 butts against guide ribs 510 shown in FIG. 14. Spring 150 continues to act on plunger 140 and thus on bung 128 so that bung 128 now moves in distal direction with respect to syringe 120 until stop member 144 is stopped by the proximal end of syringe 20. The drug 122 is thus injected into the patient's skin.

The user would then withdraw the injection device from the skin and dispose of the device.

Figure 14:
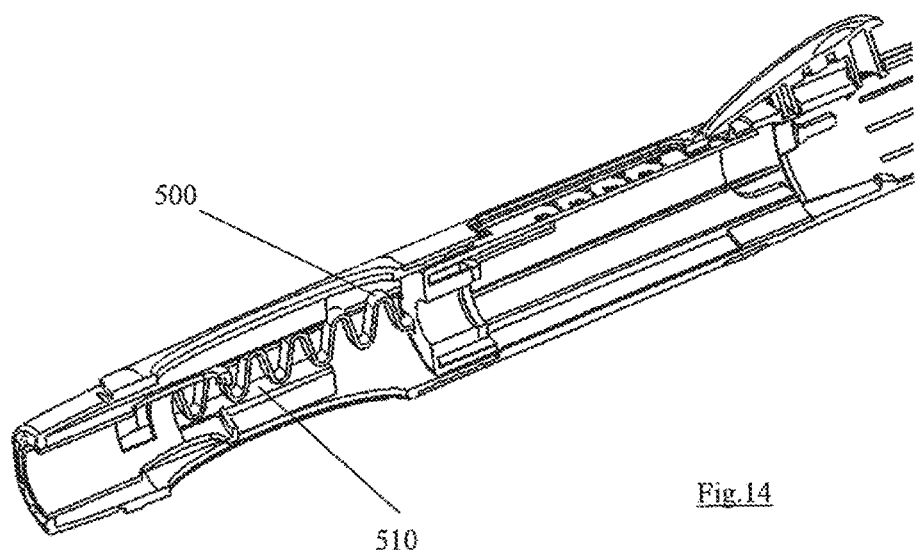
FIG. 14 shows a perspective view of a longitudinal section through part of the body of the embodiment shown in FIG. 3.
Figure 15:
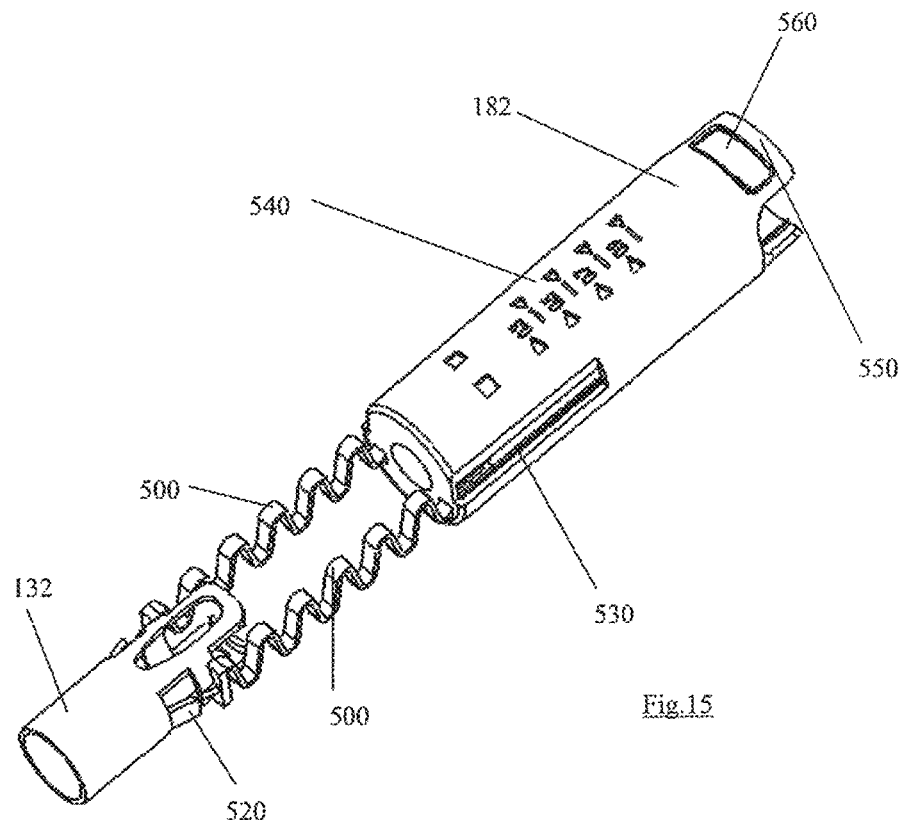
FIG. 15 shows a perspective view of a syringe carrier assembly for use in the embodiment shown in FIG. 3.
Figure 16:
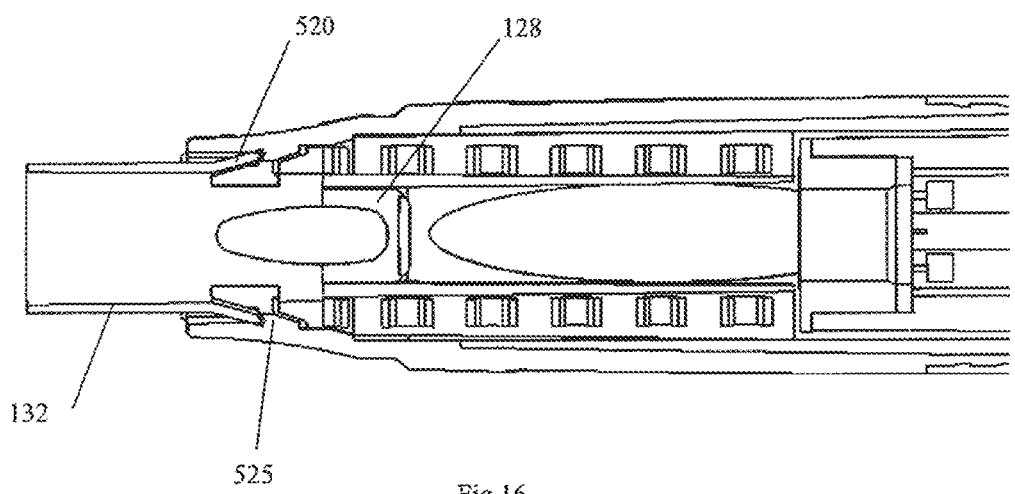
FIG. 16 shows a longitudinal section through part of the embodiment of FIG. 3.

As shown more clearly in FIGS. 14 to 16, the needle guard 132 is connected to the syringe carrier 182 by two syringe carrier springs 500. These two compression springs are located laterally alongside syringe 120. They are preferably integrally moulded with one, or preferably both, with the needle guard 132 and the syringe carrier 182. When the syringe carrier 182 moves in proximal direction during the injection operation the syringe carrier springs 500 are compressed and thus bias needle guard 132 in distal direction. Needle guard 132 can however not move in distal direction during the injection operation since it is held against the patient's skin. However, once the injection device has been removed from the patient's skin the syringe carrier springs 500 push needle guard 132 in distal direction so that its distal end projects more forward in distal direction than the distal end of needle 126 so that the needle is surrounded by needle guard 132. Needle guard 132 is laterally provided with lockout legs 520 which are arranged to co-operate with housing barbs 525 (FIG. 16) so that needle guard 132 is prevented from movement in proximal direction once lockout legs 520 have moved past housing barbs 525. This helps to protect the user from accidental injury.

As shown in FIG. 14, guide ribs 510 are provided laterally with respect to the syringe carrier springs 500 so as to guide them and to ensure that they reliably move the needle guard 132 in distal direction at the end of the injection operation.

FIG. 15 shows two further features of the injection device. Firstly, one or more cut outs 530 are provided laterally in the distal half of syringe carrier 182 which are arranged to accept corresponding ribs formed on the interior surface of the housing. This prevents the syringe carrier from rotating within the housing.

Secondly, several dose indicator windows 540 are provided in the syringe carrier 182. The dose indicator windows 540, in the embodiment shown in FIG. 15 consisting of small triangles, are individually "highlighted" if, as is preferred, the lateral surface of stop member (and dose indicator) 144 has an easily distinguishable colour, for example red. Dose indicator 144 may be moulded in that colour, or painted. As the dose indicator 144 passes underneath the triangles 540 the dose is indicated by that dose indicator window 540 which is at the same axial position as the dose indicator 144. Numbers or other symbols may be marked on the syringe carrier next to the dose indicator windows 540.

With reference to FIG. 11, it is particularly preferred that the distal end of plunger 140 is not threaded, i.e. has a non-threaded portion 400. This helps to achieve a more even pressure distribution at the interface between the distal end of plunger 140 and the proximal surface of bung 128 when compared with embodiments where the distal portion of plunger 140 is threaded as well.

It is particularly preferred that dose indicator 144 is moulded (in situ) onto plunger 140. The composition of dose indicator 144 is preferably different from that of plunger 140 so that the two parts do not bond during the moulding process. Moulding the dose indicator 144 onto the plunger 140 has three advantages. Firstly, with the distal end of plunger 140 being non-threaded, it is essentially impossible to thread dose indicator 144 onto plunger 140 from its distal end. Secondly, even if all of the plunger shaft was threaded, moulding the dose indicator 144 onto plunger 140 may make it easier to place the dose indicator 144 at the correct initial position along plunger 140. Thirdly, since it is preferred to form the thread of plunger 140 as a multi-start thread it might be more difficult to find the "correct" thread start for dose indicator 144 if it was threaded onto the plunger shaft from the distal end of the plunger 140. Moulding the dose indicator 144 onto the plunger 140 overcomes this problem.

The initial restrictions on the movement of priming button 200 of the second embodiment will now be described.

The priming button is provided (see FIG. 11) with a ring 245, which projects radially outwardly from the priming button 200. This ring 245 is circumferentially interrupted by a transit lock recess 230 and an adjoining gateway 240. The extent of the transit lock recess 230 in circumferential direction is larger than that of gateway 240. In a preferred embodiment the transit lock recess extends over an angle of about 30°. A priming button locking rib 270 (see FIG. 13) is provided on the internal surface of proximal main housing portion 111. This priming button locking rib 270 can pass through the similarly shaped and dimensioned gateway 240. The priming button locking rib 270 can, however, only pass through gateway 240 if these are aligned. In the initial condition of the injection device the priming button locking rib 270 is mis-aligned with gateway 240. However, the proximal end of priming button locking rib 270 is initially positioned within transit lock recess 230, near that circumferential end of transit lock recess 230 which in FIG. 11 is uppermost. Since a portion of ring 245 butts against the proximal end surface of priming button locking rib 270 the priming button 200 cannot be moved in distal direction. The priming button 200 can, however, be pivoted over an angle of about 30° (corresponding to the length of the transit lock recess) until the gateway 240 is aligned with priming button locking rib 270.

A priming alignment arrow 205 (see FIG. 3) is provided on the priming button to indicate that the priming button has been pivoted into the correct position for priming.

A corresponding mark can be provided on proximal main housing portion 111 with which arrow 205 can be aligned.

Once the priming button 200 has been pivoted the priming operation can be performed.

During the priming operation the priming button 200 is moved in distal direction up to a fixed stop so that the proximal end of ring 245 passes to a position just distal to the distal end of priming button locking rib 270. The gateway 240 and the distal portion of priming button locking rib 270 have a generally trapezoidal shape, their extent at their distal end being larger than at their proximal end. In particular, the width of the proximal end of gateway 240 is smaller than the width of the distal end of priming button locking rib 270 so that the priming button 200 cannot be moved in proximal direction towards the initial condition once the priming operation has been performed. As priming button locking rib 270 passes through gateway 240 the gateway 240 widens slightly. To this end the ring 245 is slightly flexible.

One or more such transit lock recesses 230, priming button locking ribs 270 and gateways 240 may be provided around the circumference of the proximal main housing portion 111 and the priming button 200, for example three.

In the second embodiment the trigger including the firing pin 320 and the syringe carrier release pin 310 is preferably a unitary moulded part. The trigger 300 of the second embodiment is arranged such that it releases bridge portion 550 from tooth 570 and (almost) simultaneously fires the device by firing pin 320 pressing down on firing block 210. While it is preferred that firing block 210 is pressed down substantially simultaneously with syringe carrier 182 being released, this is not essential. The pressing down of firing block 210 may also occur with some delay after release of the syringe carrier 182. However, in the injection device according to the second embodiment it is ensured that the syringe carrier 182 is released at the latest when compression spring 150 moves plunger 140 in distal direction.

It is worth noting that in the second embodiment it is the trigger 300 which both releases syringe carrier 182 and fires the injection device. In contrast to some prior art injection devices, the release of the syringe carrier does not cause plunger 140 to move in distal direction, nor does the movement of the plunger in distal direction cause the release of the syringe carrier 182. It is the trigger 300 which causes both these actions without these two actions influencing each other.

Figure 17:
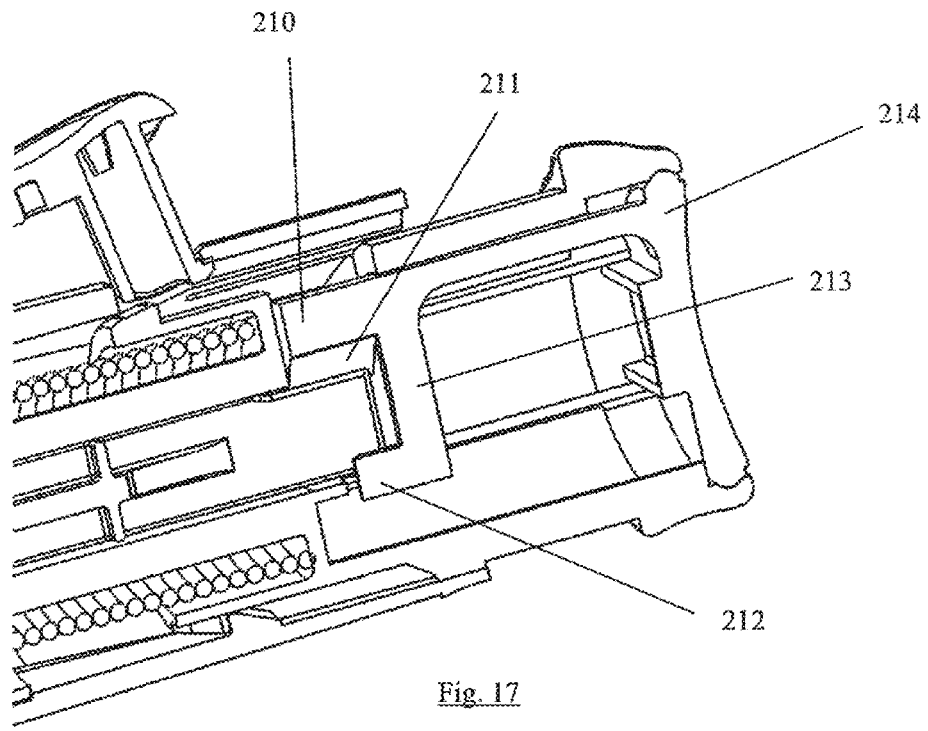
FIG. 17 shows a perspective view of a longitudinal section through the proximal portion of an injection device according to a third embodiment.
Figure 18:
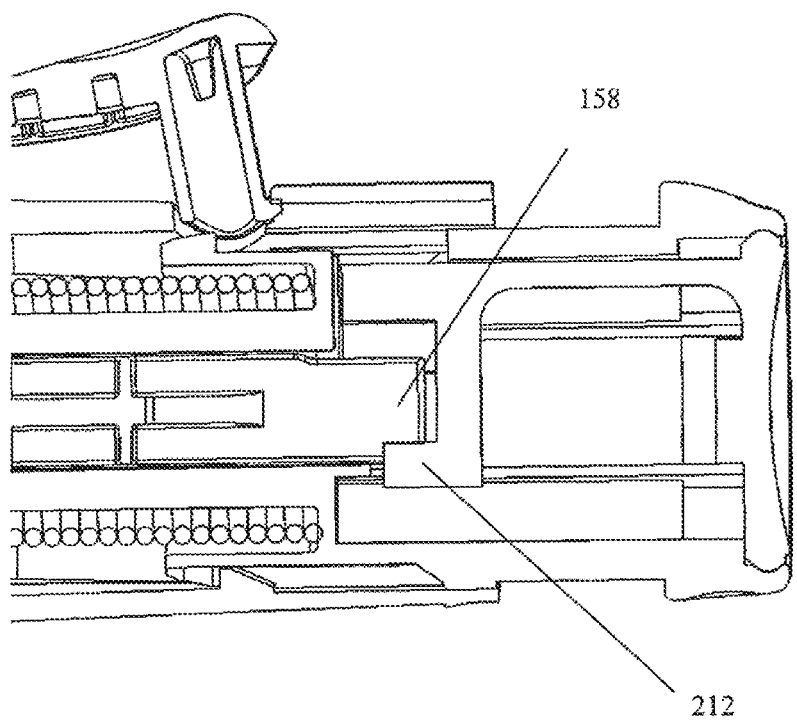
FIG. 18 shows a longitudinal section through the portion shown in FIG. 17.

A third embodiment will now be described. This is closely based on the second embodiment, and therefore only the differences will be explained here. The sectional view shown in FIG. 18 and, perspectively, in FIG. 17, is very similar to the view shown in FIG. 8. The firing block 210 is again formed with a "V" shaped profile 211 for squeezing together the proximal ends of fingers 158 of the plunger 140. However, trim cap 214 of the third embodiment is provided with a transversal portion 213 which is attached to firing block 210 and extends transversely across the injection device. A block 212 extends in distal direction from transversal portion 213 and partly projects into the space between the proximal ends of fingers 158 of the plunger 140. Block 212 thus prevents, in the initial and in the primed condition, the proximal ends of the fingers 158 of plunger 140 from moving towards each other, for example as might happen if the injection device was dropped. When the trigger is pivoted inward and firing pin 320 acts on firing block 210, block 212 moves with firing block 210 so that it no longer projects into the space between the proximal ends of fingers 158 of plunger 140. Thus the injection device can be fired properly by means of trigger 300, but an accidental firing is essentially prevented.

Whilst in the description of the preferred embodiment reference has been made to a syringe carrier 82 and 182, in the claims the term "container carrier" is used. This is to take into account that, as mentioned above, the invention may be equally applicable to devices which deliver a substance from a container which is not necessarily a syringe.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. A substance delivery device for use with a syringe (120) containing a substance, the device comprising:
 a syringe carrier (182), the syringe carrier (182) extending in a longitudinal direction and configured to carry the syringe;
 a housing having a longitudinal axis extending in the longitudinal direction and having a distal end (113) and a proximal end (111), the syringe carrier (182) being located within the housing;
 a user-removable safety cap (130) located at the distal end of the housing (113), wherein with the syringe carried by the syringe carrier, the safety cap surrounds and protects a needle extending from a distal end of the syringe; and
 a combined priming button and dose dial (200) located at the proximal end (111) of the housing and extending outward from a proximal endmost portion of the housing, the priming button and dose dial (200) having an initial non-primed position and a primed position, the priming button and dose dial (200) being movable, in the longitudinal direction, from the non-primed position and a primed position, wherein,
 i) during a priming operation, the priming button and dose dial (200) is movable, through a priming distance in the longitudinal direction, from the non-primed position to the primed position, primes the syringe, and
 ii) during a dose-setting operation, the priming button and dose dial (200) is a rotatable around the longitudinal axis to set a dose of the substance to be discharged from the syringe.

2. The substance delivery device of claim 1, further comprising impeding elements that obstruct a path of rotary travel of the priming button and dose dial (200) around the longitudinal axis when the priming button and dose dial (200) is in the non-primed position and before the priming button and dose dial (200) moves from the non-primed position to the primed position, wherein with the priming button and dose dial (200) in the primed position, the impeding elements allow delivery of the substance from the syringe.

3. The substance delivery device of claim 1, further comprising impeding elements that obstruct a path of travel of the priming button and dose dial (200) that prevents delivery of the substance from the syringe when the priming button and dose dial (200) is in the non-primed position and before the priming button and dose dial (200) moves from the non-primed position to the primed position, wherein with the priming button and dose dial (200) in the primed position, the impeding elements allow delivery of the substance from the syringe.

4. The substance delivery device of claim 2,
wherein the impeding elements further obstructs a path of travel of the priming button and dose dial (200) that prevents delivery of the substance from the syringe when the priming button and dose dial (200) is in the non-primed position and before the priming button and dose dial (200) moves from the non-primed position to the primed position, and
wherein with the priming button and dose dial (200) in the primed position, the impeding elements allow delivery of the substance from the syringe.

5. The substance delivery device of claim 1, wherein the priming button and dose dial (200) is rotatable around the longitudinal axis to set a dose of the substance to be discharged from the syringe only when the priming button and dose dial (200) is in the primed position.

6. The substance delivery device of claim 1, wherein, with the syringe carried by the syringe carrier (182), the syringe can only be moved in a distal direction when the syringe carrier (182) moves in distal direction.

7. The substance delivery device of claim 1, further comprising a trigger (300) mounted to the housing, the trigger operatively connected to trigger the delivery of the substance from the syringe.

8. The substance delivery device of claim 1, further comprising an obstruction, wherein in the non-primed position, the priming button and dose dial (200) is held slideably within the proximal end (111) of the housing, and the obstruction blocks a path of travel for rotary angular movement of the priming button and dose dial (200).

9. The substance delivery device of claim 8, wherein carrying out the priming operation moves the obstruction out of the path of travel of the priming button and dose dial (200), thereby allowing the rotary angular movement of the priming button and dose dial (200) and the dose-setting operation.

10. The substance delivery device of claim 8, further comprising a trigger (300) mounted to the housing, the trigger operatively connected to trigger the delivery of the substance from the syringe,
wherein when the priming button and dose dial (200) is in the non-primed position, a distal portion of the priming button and dose dial (200) blocks a movement path of the trigger and thereby blocks the trigger from triggering delivery of the substance from the syringe.

11. The substance delivery device of claim 9, further comprising a trigger (300) mounted to the housing, the trigger operatively connected to trigger the delivery of the substance from the syringe,
wherein carrying out the dose-setting operation moves the distal portion of the priming button and dose dial (200) from blocking the a movement path of the trigger to thereby allow user-operation of the trigger to trigger delivery of the substance from the syringe.

12. The substance delivery device of claim 1, further comprising a trigger (300) pivotally mounted to the housing, the trigger operatively connected to trigger the delivery of the substance from the syringe,
wherein, wherein when the priming button and dose dial (200) is in the non-primed position, a distal portion of the priming button and dose dial (200) blocks a movement path of the trigger and thereby blocks the trigger from triggering delivery of the substance from the syringe.

13. The substance delivery device of claim 1, wherein,
in the non-primed position, the priming button and dose dial (200) is held slideably within the proximal end (111) of the housing with longitudinal movement toward the distal end of the housing being blocked, and a path of travel for rotary angular movement being restricted to a first angular movement.

14. The substance delivery device of claim 13, wherein,
with the priming button and dose dial (200) in the non-primed position, user movement of the priming button and dose dial (200) through the first angular movement, allows limited longitudinal movement of the priming button and dose dial (200) toward the distal end of the housing thereby allowing the priming operation.

15. The substance delivery device of claim 14, wherein,
prior to the priming operation where the priming button and dose dial (200) is moved through the priming distance in the longitudinal direction, from the non-primed position to the primed position, further rotary angular movement of the priming button and dose dial (200) beyond the first angular movement is blocked, and
when the priming button and dose dial (200) is in the primed position, further rotary angular movement of the priming button and dose dial (200) beyond the first angular movement is unblocked, thereby allowing the dose-setting operation by the user rotating the priming button and dose dial (200) around the longitudinal axis to set the dose of the substance to be discharged from the syringe.

16. The substance delivery device of claim 15, wherein,
prior to carrying out the dose-setting operation, delivery of the substance to be discharged from the syringe is blocked, and
carrying out the dose-setting operation unblocks the delivery of the substance to be discharged from the syringe.

17. The substance delivery device of claim 1, further comprising impeding elements that obstruct a path of travel of the priming button and dose dial (200) so that prior to the priming operation, and prior to carrying out the dose-setting operation, delivery of the substance to be discharged from the syringe is blocked, and
sequentially carrying out the priming operation and then the dose-setting operation unblocks the delivery of the substance to be discharged from the syringe.

18. The substance delivery device of claim 1, further comprising a trigger (300) mounted to the housing, the trigger operatively connected to trigger the delivery of the substance from the syringe,
wherein when the priming button and dose dial (200) is in the non-primed position, a distal portion of the priming button and dose dial (200) blocks a movement path of the trigger and thereby blocks the trigger from triggering delivery of the substance from the syringe.

19. The substance delivery device of claim 1, wherein,
the housing comprises a mid body portion (113) held to a proximal main body portion (111), p1 the safety cap (130) is located at the distal end of the housing adjacent the mid body portion (113), a syringe viewing window (109) is located in the mid body portion (113), and a dose indicator window (116) is located in the proximal main body portion (111).

* * * * *